(12) United States Patent
Pirhonen

(10) Patent No.: US 7,241,486 B2
(45) Date of Patent: Jul. 10, 2007

(54) BONE GRAFTING MATERIALS

(75) Inventor: Eija Marjut Pirhonen, Tampere (FI)

(73) Assignee: Inion Ltd., Tampere (FI)

( * ) Notice: Subject to any disclaimer, the term of this patent is extended or adjusted under 35 U.S.C. 154(b) by 88 days.

(21) Appl. No.: 09/981,676

(22) Filed: Oct. 16, 2001

(65) Prior Publication Data

US 2002/0160175 A1 Oct. 31, 2002

(30) Foreign Application Priority Data

Apr. 26, 2001 (FI) .................................. 20010873

(51) Int. Cl.
*B32B 27/04* (2006.01)

(52) U.S. Cl. ................................ 428/297.4; 428/299.4

(58) Field of Classification Search ............. 623/16.11, 623/17.19, 11; 428/441.1, 426, 370, 372, 428/299.4, 297.4; 424/422, 423, 425

See application file for complete search history.

(56) References Cited

U.S. PATENT DOCUMENTS

| | | | | |
|---|---|---|---|---|
| 4,278,630 A | * | 7/1981 | Scheicher | .................... 264/122 |
| 4,321,042 A | * | 3/1982 | Scheicher | ................ 433/201.1 |
| 4,655,777 A | * | 4/1987 | Dunn et al. | .................... 623/16 |
| 4,735,857 A | | 4/1988 | Tagai et al. | .................. 428/388 |
| 4,794,046 A | * | 12/1988 | Nagai | ...................... 428/312.2 |
| 4,904,257 A | | 2/1990 | Mori et al. | ..................... 623/16 |
| 5,120,340 A | | 6/1992 | Ducheyne et al. | ............ 65/18.3 |
| 5,263,985 A | * | 11/1993 | Bao et al. | ....................... 623/16 |
| 5,429,996 A | | 7/1995 | Kaneko et al. | ................ 501/35 |
| 5,468,544 A | * | 11/1995 | Marcolongo et al. | ........ 428/224 |
| 5,702,761 A | * | 12/1997 | DiChiara et al. | ............ 427/181 |
| 5,711,960 A | | 1/1998 | Shikinami | .................... 424/426 |
| 5,749,720 A | * | 5/1998 | Fukuda et al. | ............... 431/285 |
| 5,769,897 A | * | 6/1998 | Harle | ........................... 424/423 |
| 5,914,356 A | | 6/1999 | Erbe | ............................ 523/114 |
| 6,054,400 A | | 4/2000 | Brink et al. | ................... 501/63 |
| 6,136,029 A | * | 10/2000 | Johnson et al. | ........... 623/16.11 |
| 6,248,344 B1 | * | 6/2001 | Ylanen et al. | ................ 424/423 |
| 6,350,284 B1 | * | 2/2002 | Tormala et al. | ........... 623/17.19 |

(Continued)

FOREIGN PATENT DOCUMENTS

FI 923561 8/1992

(Continued)

OTHER PUBLICATIONS

De Diego et al., "Tensile Properties of Bioactive Fibers for Tissue Engineering Applications," Dept. of Materials, Imperial College of Science, Technology and Medicine, London, England, *J. Biomed. Mater. Res.*, 53:199-202 (1999).

(Continued)

*Primary Examiner*—Rena Dye
*Assistant Examiner*—Carnie S. Thompson
(74) *Attorney, Agent, or Firm*—Banner & Witcoff, Ltd.

(57) ABSTRACT

The present invention relates to porous bone filling materials prepared by sintering bioactive glass fibers in order to achieve a three dimensional block with interconnecting porosity. Due to the osteoconductive properties the bioactive glass fibers, in block form are an ideal scaffold for new tissue (e.g. bone or cartilage) formation to occur. The manufacturing parameters can be adjusted to achieve porosities as high as 90 vol-%, or the manufacturing parameters can be adjusted to prepare strong porous blocks useful in load bearing application.

39 Claims, 2 Drawing Sheets

U.S. PATENT DOCUMENTS 6,451,059 B1 * 9/2002 Janas et al. .............. 623/23.51
6,517,857 B2 * 2/2003 Ylanen et al. .............. 424/422

FOREIGN PATENT DOCUMENTS

| FI | 1000103715 B | | 10/1998 |
|---|---|---|---|
| GB | 2 178 422 | | 2/1987 |
| WO | WO 86/04088 | | 7/1986 |
| WO | WO86-04088 | * | 7/1986 |
| WO | WO 97/31661 | | 9/1997 |
| WO | WO98-47465 | * | 10/1998 |
| WO | WO 00/35509 | | 6/2000 |

OTHER PUBLICATIONS

Ehrnford et al., "Bone Tissue Formation within a Sintered Micro Porous Glass Fiber Network Implanted in Extraction Sockets in the Rat," *Scandinavian J. Dental Res.*, 88(2):130-133 (1980) (with English abstract).

* cited by examiner

BONE GRAFTING MATERIALS

FIELD OF THE INVENTION

The present invention relates to bone grafting materials prepared from glass fibers, preferably bioactive glass fibers by sintering the fibers to form a porous three dimensional block for filling in a defect or hollow portion of bone. In more detail the present invention relates to a block prepared by sintering glass fibers, preferably bioactive glass fibers together to form a porous three dimensional block. The prepared block is an ideal scaffold for new tissue (e.g. bone or cartilage) formation to occur due to the osteoconductive properties of the bioactive glass fibers.

BACKGROUND OF THE INVENTION

In surgical and orthopedic treatments, prosthesis operations are often required for filling in defects or hollow portions of bone which may result from fracture of bone or surgical removal of bone tumor. Also in the field of dental surgery, similar denture operations are often required for filling in spoiled void portions in maxilla or mandible resulting from pyorroea alveolaris. It has been a common practice to harvest bone from donor site, for example from the iliac crest of the patient to fill up the defect or hollow portion of bone and thereby to promote the regeneration of the bone tissue. However, to perform such an operation normal, undamaged bone tissue must be picked up from an unspoiled portion. This operation causes additional pain to the patient and is, in addition, a very troublesome procedure. Moreover, when the volume of the defect or void in the patient's bone is large, the amount of bone obtainable from the patient's own body is not always adequate to fully fill in the defect or void. In such cases it is inevitable to use a substitute for the patient's own bone tissue. Even though the same sort of bone tissue has been used as the substitute, the implanted substitute may be rejected by the living tissue due to the foreign body rejection reaction (by the immune system). For these reasons the post-operation recovery of the defect is not always satisfactory. Accordingly, such an operation has not yet been recognized as fully satisfactory in practice.

There is therefore a demand for an artificial material which has excellent compatibility with living tissues when filled in a defect or hollow portion of bone to facilitate formation of bone within and at the vicinity of the defect and to promote repair and recovery of the structure and function of the once damaged bone tissue.

A variety of metal alloys and organic materials have been used as the substitute for the hard tissues in the living body. However, it has been recognized that these materials tend to dissolve or otherwise deteriorate in the environment of living tissue and that these materials are toxic to the living body and cause so called foreign body rejection reaction. Ceramic materials have been used because of their excellent compatibility with the living body and because they are typically free of the aforementioned difficulties. Artificial bones and teeth have been developed from ceramic materials, particularly alumina, carbon or tricalcium phosphate or from sintered masses or single crystal of hydroxyapatite which have superior compatibility with living body. These embodiments have attracted a good deal of the public attention.

However, the conventional ceramic implant materials have a common disadvantage in that they are inherently too hard and brittle. Therefore these known ceramic materials are not fully satisfactory in practical use. There have been attempts to fill defects in bone with a sintered ceramic block or a ceramic block of single crystal form. However, since uneven gaps or interstices are formed between the block and the bone tissue, the object of fully filling in the void in the bone cannot be attained. On the other hand, when alumina is used as the filler, it acts as a stimulant to cause absorption of bone at the vicinity of the implanted filler due to the fact that alumina is much harder than the bone tissue. Furthermore, it has not been clarified what properties a ceramic material should possess to suppress the foreign body rejection reaction and to improve the compatibility with living body as well as promote formation of new bone.

Heimo Ylänen (Doctoral Thesis, Turku, Finland 2000) has studied bone ingrowth into porous bodies made by sintering bioactive glass microspheres. He has found out that rigid porous bioactive glass implants provide an environment that promotes, throughout the whole implant, an extended incorporation of new bone into space between the sintered bioactive microspheres. As a result the implant is quickly and firmly bonded to the host bone. In the studies it is also noted that the in vitro rate of the reactions inside the porous glass implant is higher than the non-porous glass rods made from the same bioactive glass. The block sintered from bioactive glass spheres is brittle and breaks easily if load is applied to it. Another drawback with blocks sintered from glass spheres is that the porosity is considerably low and this affects bone forming properties in this device.

Publication WO 00/35509 discloses a porous textile product made from bioactive glass and a weakly bioactive glass. Several ways to produce the textile product are suggested in the publication but there is no suggestion of sintering the bioactive glasses together.

Finnish patent 103,715 ('715 patent) discloses a composite made of bioactive material A and of non-bioactive material B or weakly bioactive material B and the materials have been sintered together to a porous composition. According to the '715 patent particles A and B are rounded, preferably spherical. In the '715 patent there is no suggestion to use glass fibers for preparing the composition.

Finnish patent application 923,561 discloses bioactive glass compositions and preparation of implants from the filaments of the said bioactive glass compositions. However, there is no teaching in the publication to sinter the filaments together.

Publication WO 97/31661 describes an osteogenic device which comprises a shapeable porous carrier body selected from hydroxyapatite, tricalcium phosphate, bioactive glass and biocoral. There is no teaching in the publication of using bioactive glass fiber.

U.S. Pat. No. 6,054,400 ('400 patent) discloses an invention which relates to novel bioactive glasses with a large working range and controlled durability. The '400 patent further discloses the use of the bioactive glasses for tissue bonding purposes in the medical or dental field, for use in biotechnology, for controlled release of agents and for tissue guiding. The filling material comprises bioactive glass in crushed form or as spherical granules. There is no suggestion in the US patent to use glass fibers.

U.S. Pat. No. 5,429,996 concerns a bone grafting material for use in medicine which is glass wool having the following composition 40–62% (w/w) $SiO_2$, 10–32% (w/w) $Na_2O$, 10–32% (w/w) CaO, 0–12% (w/w) $P_2O_5$, 0–12% (w/w) $CaF_2$, 0–21% (w/w) $B_2O_3$. The glass wool has a mean diameter of 100 μm or less. There is no suggestion of using sintered glass fibers in this publication, however.

U.S. Pat. No. 5,468,544 discloses composite materials using bone bioactive glass and ceramic fibers. In more detail in the patent is described composite structures that incorporate a bioactive material in a polymer matrix along with a structural fiber. The polymeric matrix used is a non-bioabsorbable polymeric matrix, for example polysulphone, PEEK or PEKK and the structural fiber is a carbon fiber.

U.S. Pat. No. 4,735,857 describes a fiber glass for filling in a defect or hollow portion of bone. The fiber glass comprises calcium phosphate as a main ingredient and has a negative zeta potential. The fiber glass is of long filament form or staple fiber form and the long filament form may be woven to form a woven filler, for example a cloth or gauze. In the US patent there is no suggestion of sintering the fibers.

U.S. Pat. No. 5,914,356 describes a woven filler for filling in a defect or hollow portion of bone. The woven filler is prepared by weaving fiber glass filaments which fiber glass consists essentially of calcium phosphate and has a negative zeta point as well, and of an inorganic oxide. The inorganic oxide can be alumina, silica, sodium oxide, iron oxide, magnesium oxide, kaolin or a mixture thereof. There is no teaching of sintering the glass fibers in this patent.

U.S. Pat. No. 5,711,960 describes an implant material which comprises as a base material a biocompatible bulk structure of a tri-axial or more three-dimensionally woven fabric of organic fibers, a tri-axial or more three-dimensionally knitted fabric of organic fibers or combination thereof.

U.S. Pat. No. 4,904,257 discloses a method of filling a void in a bond which comprises filling the void with a fibrous bone comprising fibers containing intact hydroxylapatite, water-soluble binder and water.

M. A. De Diego et al. (Tensile Properties of Bioactive Fibers for Tissue Engineering Applications, Journal of Biomedical Materials Research, 2000, Vol. 3,199–203) have studied tensile properties of bioactive fibers for tissue engineering applications. The tested material was 45S5 Bioglasse which is a 4-component, melt-derived bioactive glass. In the study tensile strength, elongation to fracture and Weibull's moduli of 45S5 Bioglasse is reported.

It is also known in the art that the fabrication of 3D scaffolds for skeletal reconstruction from bioceramics and biopolymers has been studied.

BRIEF DESCRIPTION OF THE INVENTION

Surprisingly it has been found that by sintering glass fibers, preferably bioactive glass fibers, the problems related to the prior art solutions can be solved. An object of the present invention is thus to provide a porous bioactive scaffold, manufactured from glass fibers, preferably bioactive glass fibers, by sintering for filling in a defect or hollow portion of bone to solve the above problems. The porous scaffold can also be prepared by sintering other bioceramic fibers for example HA (hydroxyapatite) fibers. The objects of the invention are achieved by an arrangement, which is characterized by what is stated in the independent claims. The preferred embodiments of the invention are disclosed in the dependent claims. These and other aspects of the invention are discussed below.

The invention is based on the idea of manufacturing a porous scaffold by sintering glass fibers. In a preferred embodiment of the present invention bioactive glass fibers are sintered together to form a scaffold. Bioactive glass has an excellent compatibility with the living body without causing foreign body rejection reaction, promotes early formation of new bone and unifies integrally with the growing hard tissue of the living body.

Another object of the present invention is to provide a scaffold promoting bone formation reaction in the area filled with the sintered glass fiber block, preferably with the bioactive glass fiber block, to promote recovery of the structure and function of the once damaged bone tissue.

Another object of this invention is to provide a glass fiber scaffold, preferably a bioactive glass fiber scaffold for filling in a defect or hollow portion of bone and maintain the space, even though load is applied on the scaffold.

Another object of this invention is to provide a method for preparing the porous scaffold of the present invention by sintering glass fibers, preferably bioactive glass fibers.

The above and other objects of the invention will become apparent from the following detailed description of the invention.

An advantage of the invention is that by sintering glass fibers, preferably bioactive glass fibers instead of glass microspheres, a higher strength scaffold is obtained. Also a greater porosity percentage is achieved by sintering glass fibers compared to the spheres. Without wishing to be bound by any scientific theory. The healing of the bone may be faster because the proportion of the bone in the scaffold is larger compared to the scaffolds prepared from glass spheres. Another advantage of the present invention is that if a dissolvable glass is used the final dissolving of the scaffold in the tissue is effected by the diameter of the fibers. The smaller the diameter of the fibers the faster the scaffold is dissolved in the tissue. Another advantage of the present invention is that there is a greater amount of reacting surface in the scaffold when the scaffold is prepared by sintering glass fibers, preferably bioactive glass fibers compared to the scaffold prepared by sintering glass spheres. By using a scaffold prepared by sintering glass fibers it is possible to adjust the retaining time of the scaffold in the tissue to an appropriate level.

Wound stability is a critical factor in the healing of a wound. Wound stability appears to be critical for example to the outcome of periodontal healing. If tensile forces acting on the wound margins can be controlled by wound stabilizing measures such as grafting and implant materials, specific flap adaptation and suturing techniques, or barrier membranes; the root surface-gingival flap interface may heal with connective tissue repair. Another advantage of the present invention is that when scaffolds prepared by sintering glass fibers or bioactive glass fibers are used, it seems that there are less tensile forces on the wound margins and a greater wound stability is reached. This can result in a faster wound healing.

BRIEF DESCRIPTION OF THE DRAWINGS

In the following the invention will be described in greater detail with reference to the attached drawings, in which.

DETAILED DESCRIPTION OF THE INVENTION

Figure 1:
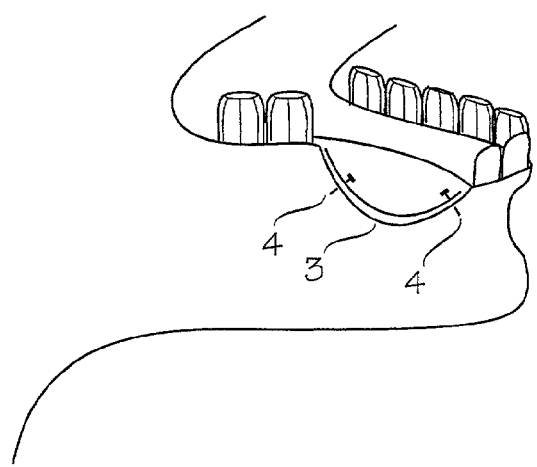
FIG. 1 shows a porous bioactive scaffold attached to a polymeric film and its application in the use of reconstructing alveolar bone, in accordance with preferred embodiments.
Figure 1:
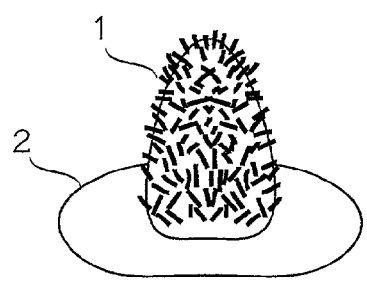
Figure 1:
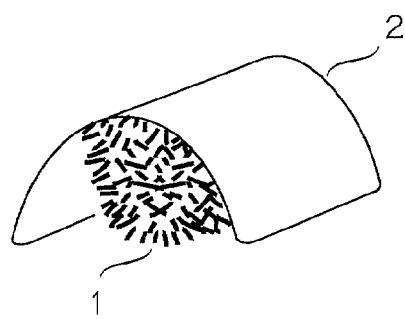
Figure 1:
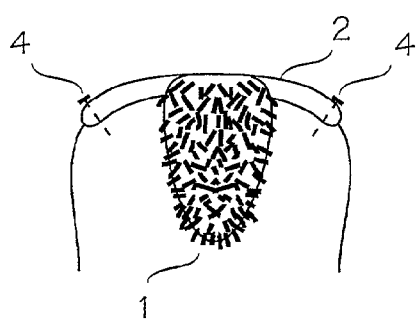

Bioactive material is a material that has been designed to induce specific biological activity.

Bioactive glass refers to any glass or glass ceramic that displays the characteristics of bioactivity. Bioactive glass is an amorphous solid that is not intrinsically adhesive and that is capable of forming a cohesive bond with both hard and soft tissue when exposed to appropriate in vivo and in vitro environments, such as simulated body fluid or tris-hydroxymethylaminomethane buffers. A cohesive bond is achieved by developing a surface layer of hydroxycarbonate apatite onto the bioactive glass through the release of ionic species from the bulk bioglass material.

Bioceramic is any ceramic, glass or glass ceramic that is used as a biomaterial and a ceramic which upon implantation is transformed into less soluble minerals. Bioactive glass is an example of a bioceramic material.

Osteoconduction is a process of passively allowing bone to grow and remodel over a surface. In osteoconduction the implant provides a biocompatible interface along which bone migrates.

Porosity refers to the volume percentage of air in a three dimensional scaffold.

Scaffold is a porous structural device that allows living tissues to grow into it. A scaffold can form a base which serves as a guide for tissue growth.

In the present invention glass fibers, preferably bioactive glass fibers are first formed by any suitable technique known to those skilled in the art e.g. by using melt spinning technique. The fibers are then chopped into desired length. Lump of fibers is then heated in an oven so that fibers are sintered together and a porous three-dimensional block is formed. The properties of block, i.e. porosity, pore size and compressive strength can be adjusted to a desired level by adjusting fiber diameter, sintering time and sintering temperature. The porous three-dimensional block can also be prepared by sintering bioceramic fibers.

In another embodiment of the present invention the sintering of the glass fibers, preferably bioactive glass fibers is performed under load. Under load means that a weight is applied onto the fibers during the sintering. Sintering under load results in a more homogenous structure of the scaffold.

By sintering glass fibers, preferably bioactive glass fibers, a porous, osteoconductive scaffold can be formed. By optimizing the processing parameters the degree of porosity can be controlled. Porosities as high as 90 vol % can be achieved when the glass fibers are sintered together as described herein. Compression strength of the scaffold can be optimized to be from 5 to 25 MPa, and preferably over 20 MPa, which is stated to be the requirement for load bearing purposes of the scaffold. The optimization is preferably performed by increasing fiber diameter, sintering temperature and sintering time. A sintered body from glass fibers, preferably bioactive glass fibers is considerably soft and by altering the processing parameters, different kinds of products with different kind of properties can be formed.

In a preferred embodiment of the present invention a porous scaffold made by sintering glass fibers, preferably bioactive glass fibers can be attached to a biocompatible polymeric film such that the porous scaffold has a barrier property on its side. This apparatus can be used for example with guided bone regeneration where barrier effect is required to avoid soft tissue ingrowth in the area where new bone formation is required. Another application of the apparatus is in regeneration of cartilage tissue. The porous scaffold sintered from glass fibers, preferably from bioactive glass fibers is able to form a matrix into which cartilage tissue can grow. The other side of the scaffold with polymeric film serves as a barrier that separates the newly formed cartilage tissue from the synovial liquids.

The biocompatible film can be prepared for example of polyglycolide, polylactide, poly-β-hydroxybutyric acid, polydioxanone, polyvinylalcohol, polyesteramine, their copolymers or polymer blends thereof.

In another preferred embodiment of the present invention the glass fibers, preferably bioactive glass fibers can be sintered together under compression load. The compression load used is approximately 10 kPa.

In another preferred embodiment of the present invention bioactive agents can be used in combination with the sintered porous scaffold to promote new tissue, e.g. bone formation. In such a case the porous scaffold made from bioactive glass fibers can act as carrier for bioactive agents. The biologically active agent is selected from the group consisting of anti-inflammatory agents, antibacterial agents, antiparasitic agents, antifungal agents, antiviral agents, antineoplastic agents, analgesic agents, anaesthetics, vaccines, central nervous system agents, growth factors, hormones, antihistamines, osteoinductive agents, cardiovascular agents, anti-ulcer agents, bronchodilators, vasodilators, birth control agents, fertility enhancing agents and polypeptides. Preferably the bioactive agents are bone morphogenic proteins (BMP), such as OP-1, BMP-2, BMP-4 and BMP-7.

In another preferred embodiment of the present application the glass fibers, preferably the bioactive glass fibers are first coated with a biocompatible polymer prior to the sintering. The fibers are chopped and then the coated fibers are sintered to form a three dimensional scaffold. In this case the scaffold has reasonable elastic performance and can be applied in cases where elastic performance is required from the scaffold.

The bioactive glass used in this invention has the following composition about 53–about 60 wt-% $SiO_2$, about 0–about 34 wt-% $Na_2O$, about 1 about 20 wt-% $K_2O$, about 0–about 5 wt-% MgO, about 5–about 25 wt-% CaO, about 0–about 4 wt-% $B_2O_3$, about 0.5–about 6 wt-% $P_2O_5$, provided that $Na_2O+K_2O$=about 16–about 35 wt-%; $K_2O+MgO$=about 5–about 20 wt-% and MgO+CaO=about 10–about 25 wt-%. Preferably the bioactive glass has the following composition 53 wt-% $SiO_2$, 6 wt-% $Na_2O$, 12 wt-% $K_2O$, 5 wt-% MgO, 20 wt-% CaO, 0 wt-% $B_2O_3$ and 4 wt-% $P_2O_5$. The preferred composition is referred in this context as glass 13-93 prepared by Abmin Technologies.

The chopped fibers have a length from about 2 to about 30 mm, and preferably the length of the fibers is approximately from about 5 to about 15 mm. By controlling the length of the fibers the size of the pores can be adjusted to a desired level.

The fibers have a diameter of about 0.010–about 1.0 mm and preferably have a diameter of about 0.030 to about 0.300 mm. By altering the diameter of the fibers the rate of dissolving can be controlled. Lower sintering temperatures can be used for fibers with smaller diameter and a more porous scaffold is received. By altering the processing parameters the properties of the scaffold can be adjusted to desired level and for example a scaffold which is easily formable for example with a knife can be prepared.

Sintering temperatures of the present invention for bioactive glass fibers are from about 300° C. to about 1500° C., preferably from about 600° C. to about 700° C., and most preferably from about 630° C. to about 680° C.

When fibers coated with biocompatible polymers are sintered, the sintering temperature depends on the softening point of the coat polymer. When biocompatible polymers are used the sintering temperature is from about 50° C. to about 300° C., and preferably from about 100° C. to about 200° C.

Suitable biocompatible polymers are for example polyglycolide, polylactide, poly-β-hydroxybutyric acid, polydioxanone, polyvinylalcohol, polyesteramine, their copolymers and polymer blends thereof.

The thickness of the polymer coating on the fibers is from about 1 to about 200 μm, preferably from about 5 to about 30 μm.

The preferred sintering time in this invention when sintering glass fibers, preferably bioactive glass fibers, is from about 1 to about 120 minutes and preferably from about 5 to about 30 minutes. The sintering time of the present invention when sintering glass fibers coated with polymers, preferably bioactive glass fibers coated with polymers is from about 1 to about 120 minutes and preferably from about 5 to about 30 minutes.

By altering the sintering parameters, i.e. sintering temperature, sintering time, length of the fibers, diameter of the fibers, etc., the properties of the formed scaffold can be adjusted to desired levels. For example, the compression strength of the scaffold can be increased when thicker fibers and a higher sintering temperature are used. The formability of the scaffold can be improved when thinner fibers are used and the sintering temperature is in the lower end of the softening area of the glass.

By sintering glass fibers, preferably bioactive glass fibers a scaffold is formed which has a porosity of about 5 to about 95 volume-% and preferably from about 50 to about 90 volume-%.

The load bearing capacity of the prepared scaffold is characterized by the compression strength. When sintering glass fibers, preferably bioactive glass fibers, a scaffold is obtained which has excellent load bearing properties. The compression strength of the scaffold of this invention is from about 5 to about 25 MPa and preferably over or greater than 20 MPa.

FIG. 1 shows one preferred embodiment of the present invention where sintered porous glass fiber scaffold, preferably a bioactive glass fiber scaffold, 1 is attached to a polymeric film 2, e.g. by sintering or by processing under heat and pressure. The film with porous scaffold can be used, for example as a membrane in Guided Bone Regeneration procedures or Guided Tissue Regeneration procedures, where the membrane is used as a barrier to avoid soft tissue ingrowth, to enhance the regeneration of bone tissue (or periodontal tissues). FIG. 1 also shows that the film 2 which has a scaffold 1 attached to it can be bent and formed into a desired shape. FIG. 1 illustrates an example of using scaffold 1 and the film 2 in reconstructing a defect in alveolar bone 3. The scaffold 1 and the film 2 are attached to the defect with small nails 4 or other comparable apparatus suitable for attachment of the scaffold to a defect.

Figure 2:
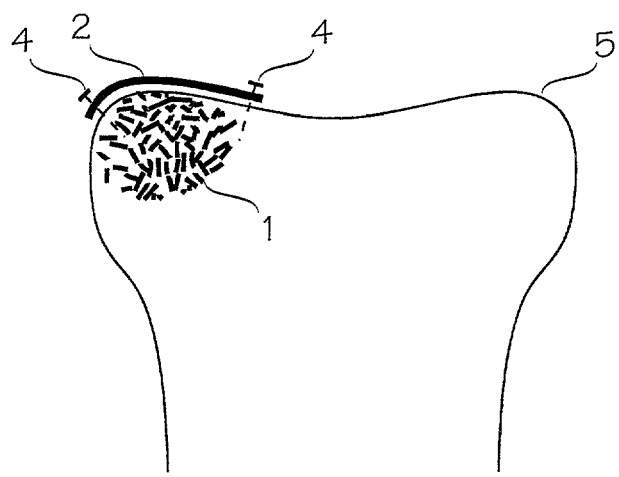
FIG. 2 shows the use of the porous bioactive scaffold attached to a polymeric film in filling in a bone defect, in accordance with preferred embodiments.

FIG. 2 shows an example of the use of the scaffold 1 and the membrane 2 in filling in a defect in a bone 5. The scaffold and the film can be attached to the bone with small nails 4 or other comparable apparatus suitable for attachment of the scaffold to a defect.

Figure 3:
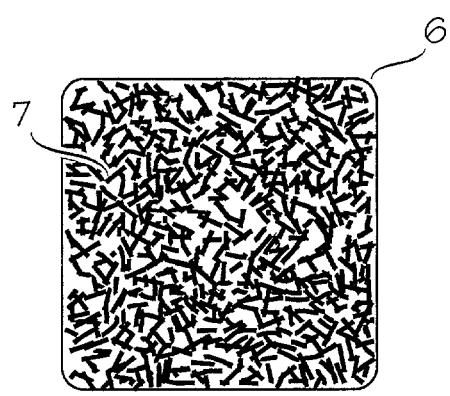
FIG. 3 shows a mat of the sintered bioactive glass fibers attached to a membrane, in accordance with preferred embodiments.

FIG. 3 illustrates another preferred embodiment of the present invention in which a sintered mat of the glass fibers 7, preferably a sintered mat of the bioactive glass fibers is attached to a membrane 6. This device can be used in guided tissue regeneration or in guided bone regeneration.

Figure 4:
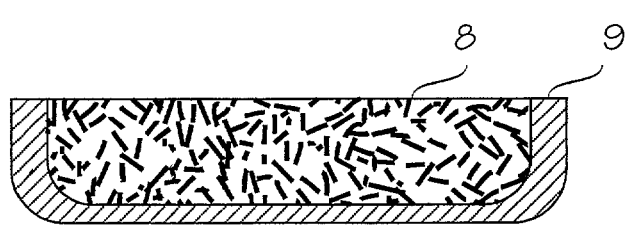
FIG. 4 illustrates the sintering of the bioactive glass fibers in a mould form, in accordance with preferred embodiments.

In one embodiment of the present invention, as illustrated in FIG. 4, the sintering of the glass fibers 8, preferably bioactive glass fibers is performed in a mold form 9 and a three dimensional scaffold of desired form is then obtained. When a three dimensional scaffold is obtained there is no need to machine the scaffold after the sintering of the fibers.

It will be obvious to a person skilled in the art that, as the technology advances, the inventive concept can be implemented in various ways. The invention and its embodiments are not limited to the examples described above or below but may vary within the scope of the claims.

EXAMPLES

Example 1

Bioactive glass fibers were formed from glass 13-93 (prepared by Abmin Technologies) by melt spinning. The piece of glass with mass of 150 g was placed into a platinum crucible, which had an orifice with diameter of 3.5 mm at the bottom. The crucible was then placed into the furnace (LINDBERG/BLUE CF56622C, by LINDBERG/BLUE, NC, U.S.A), which had opening at the bottom. Furnace was then heated up to a temperature of 960 C. As the glass melted it started to run from the orifice and it was drawn with a specially designed spinning roll. The speed of the roll was set to 200 mm/s. Obtained glass fiber was taken out from the roll. The diameter of the fiber was 0.175 mm (+/−0.025 mm). Fibers were then chopped to a length of 10 mm (+/−2 mm) by using scissors.

2 grams of the chopped fibers were placed on to a steel plate and the plate with glass fibers was placed into furnace. The furnace was slowly heated up to a temperature of 655° C. This was retained for 30 minutes and after that the furnace was cooled down.

From the obtained porous block three rectangular blocks were shaped by saw in order to measure the porosity and compression strength of the blocks.

The outer dimensions and the weight of each block were measured. The calculated mean porosity of the blocks was 26 vol-% glass (+/−5%) and 74 vol-% of air.

The compression strength of the blocks was measured by using an Instron materials testing machine. The mean strength of 24.4 MPa (Stdev 3.8 MPa) was obtained.

Example 2

Bioactive glass fibers were formed from glass 13-93 by melt spinning as described in Example 1. The diameter of the fibers was 0.075 mm (+/−0.025 mm).

Fibers were then chopped to the length of 15 mm (+/−2 mm) by using scissors. Chopped fibers were placed on to a steel plate, and the plate with glass fibers was placed into a furnace. The furnace was slowly heated up to a temperature of 650° C. and the temperature was retained there for 30 minutes after which the furnace was cooled down.

From the obtained porous block three rectangular blocks were shaped with a surgical knife in order to measure porosity.

The outer dimensions and the weight of each block were measured. The calculated mean porosity of the blocks was 11 vol-% glass (+/−7%) and 89 vol-% of air.

Example 3

Bioactive glass fibers from glass 13-93 with diameter of 0.1 mm (+/−0.03 mm) were formed by melt spinning as described in Example 1. Formed fibers were coated with viscous solution, which contained 5 grams of biodegradable polymer PLA (70L/30DL) and 100 ml chloroform as a solvent. Fibers were coated as part of the spinning process (as described in Example 1) by dipping fibers into the solution prior to winding them up with spinning roll. The speed of the spinning roll was set to 200 mm/s.

Coated fibers were chopped by using scissors into a length of 15 mm (+/−2 mm). Chopped fibers were placed on to a steel plate and the plate with glass fibers was placed in a furnace. The furnace was slowly heated to a temperature of 140° C. for 5 minutes after which the furnace was cooled down. The obtained body had porosity of approximately 15 vol-% glass, 2 vol-% of polymer and 82 vol-% of air. The body was slightly flexible and did not break when bent.

Example 4

A porous block was formed from bioactive glass fibers as expressed in Example 1 and the block was machined to have cylindrical shape with diameter of 15 mm and height of 10 mm. A polymeric film (made of polylactide) with thickness of 0.5 mm was formed by compression molding by placing 3 grams of polylactide granules between the heated plates of custom made compression molding machine. The temperature of the plates was 190° C. After placing the granules between the plates compressive pressure of 100 bars was applied. After applying pressure for one minute the cooling unit was turned on. As soon as the plates reached temperature of 40° C. the pressure was released and formed film was removed from the machine. From the compressed film a circular shape with diameter of 30 mm was cut.

The circular shape polymeric film was then attached to the porous block formed from bioactive glass fibers by using compression moulding, as follows. The plates of compression moulding machine were heated to the temperature of 180° C. The parts were placed between the hot plates so that the porous block was placed right into middle of polymeric film. After 3 minutes, a pressure of 1 bar was applied and a cooling unit was then swithced on.

After the plates were cooled to 30° C., the resulting product was removed from the press. The resulting product includes the block firmly attached to the polymer film.

The invention claimed is:

1. A sintered scaffold material comprising bioactive glass fibers sintered together to form the scaffold material, wherein the scaffold material has a porosity of between about 50 volume % and about 90 volume %, and wherein the scaffold material has a pore size sufficient to allow ingrowth of tissue.

2. The scaffold of claim 1, wherein the glass fibers are sintered together at a temperature from between about 300° C. to about 1500° C.

3. The scaffold of claim 1, wherein the glass fibers are sintered together at a temperature from between about 600° C. to about 700° C.

4. The scaffold of claim 1, wherein the glass fibers are sintered together at a temperature from between about 630° C. to about 680° C.

5. A sintered glass scaffold comprising glass fibers sintered together to form the scaffold, wherein the fibers have a coating of one or more biocompatible polymers or copolymers.

6. The scaffold of claim 5, wherein the glass fibers comprise bioactive glass fibers.

7. A sintered glass scaffold comprising glass fibers sintered together to form the scaffold, wherein the fibers have a coating of one or more biocompatible polymers or copolymers, and wherein the biocompatible polymer is selected from the group consisting of polyglycolide, polylactide, poly-β-hydroxybutyric acid, polydioxanone, polyvinylalcohol, polyesteramine, their copolymers and polymer blends thereof.

8. The scaffold of claim 5, wherein the coating has a thickness of about 1 μm to about 200 μm.

9. The scaffold of claim 5, wherein the coating has a thickness of from about 5 μm to about 30 μm.

10. The scaffold of claim 6, wherein the glass fibers coated with a polymer or copolymer are sintered at a temperature of between about 50° C. to about 300° C.

11. The scaffold of claim 5 wherein the glass fibers coated with a polymer or copolymer are sintered at a temperature of between about 100° C. to about 200° C.

12. A sintered scaffold material comprising fibers, wherein the glass fibers comprise bioactive glass having a composition of about 53 to about 60 wt-% $SiO_2$, about 0 to about 34 wt-% $Na_2O$, about 1 to about 20 wt-% $K_2O$, about 0 to about 5 wt-% $MgO$, about 5 to about 25 wt-% $CaO$, about 0 to about 4 wt-% $B_2O_3$, about 0.5 to about 6 wt-% $P_2O_5$, wherein $Na_2O$ in combination with $K_2O$ is present in an amount between about 16 to about 35 wt-%; $K_2O$ in combination with MgO is present in an amount between about 5 to about 20 wt-% and MgO in combination with CaO is present in an amount between about 10 to about 25 wt-%.

13. A sintered glass scaffold comprising glass fibers, wherein the glass fibers comprise bioactive glass having a composition of about 53 wt-% $SiO_2$, about 6 wt-% $Na_2O$, about 12 wt-% $K_2O$, about 5 wt-% $MgO$, about 20 wt-% $CaO$, about 0 wt-% $B_2O_3$ and about 4 wt-% $P_2O_5$.

14. The scaffold of claim 1 or 5, wherein the fibers prior to sintering have a length from about 2 mm to about 30 mm.

15. The scaffold of claim 1 or 5, wherein the fibers prior to sintering have a length from about 5 mm to about 15 mm.

16. The scaffold of claim 1 or 5, wherein the glass fibers are sintered for about 1 minute to about 120 minutes.

17. The scaffold of claim 1 or 5, wherein the glass fibers are sintered for about 5 to about 30 minutes.

18. The scaffold of claim 1 or 5, wherein the fibers prior to sintering have a diameter of about 0.010–1.0 mm.

19. The scaffold of claim 1 or 5, wherein the fibers prior to sintering have a diameter of about 0.030–0.300 mm.

20. The scaffold of claim 5, wherein the scaffold has a porosity of between about 5 volume % and about 95 volume %.

21. The scaffold of claim 5, wherein the scaffold has a porosity of between about 50 volume % and about 90 volume %.

22. The scaffold of claim 1, wherein the scaffold is a carrier for bioactive agents.

23. The scaffold of claim 5, wherein the scaffold is a carrier for bioactive agents.

24. A sintered scaffold material comprising bioactive glass fibers or ceramic fibers,
wherein the scaffold material has a porosity of between about 50 volume % and about 90 volume %,
wherein the scaffold material has a pore size sufficient to allow ingrowth of tissue,
wherein the scaffold is a carrier for at least one bioactive agent, and
wherein the bioactive agent is selected from the group consisting of anti-inflammatory agents, antibacterial agents, antiparasitic agents, antifungal agents, antiviral agents, anti-neoplastic agents, analgesic agents, anaesthetics, vaccines, central nervous system agents, growth factors, honnones, antihistamines, osteoinductive agents, cardiovascular agents, anti-ulcer agents, bronchodilators, vasodilators, birth control agents, fertility enhancing agents and polypeptides.

25. A sintered glass scaffold comprising glass fibers, wherein the glass fibers have a coating of one or more biocompatible polymers or copolymers, wherein the scaffold is a carrier for at least one bioactive agent, and wherein the bioactive agent is selected from the group consisting of anti-inflammatory agents, antibacterial agents, antiparasitic agents, antifungal agents, antiviral agents, anti-neoplastic agents, analgesic agents, anaesthetics, vaccines, central nervous system agents, growth factors, hormones, antihistamines, osteoinductive agents, cardiovascular agents, anti-ulcer agents, bronchodilators, vasodilators, birth control agents, fertility enhancing agents and polypeptides.

26. A sintered scaffold material comprising bioactive glass fibers or ceramic fibers,
    wherein the scaffold material has a porosity of between about 50 volume % and about 90 volume %,
    wherein the scaffold material has a pore size sufficient to allow ingrowth of tissue, and
    wherein the scaffold is a carrier for at least one bioactive agent, and wherein the bioactive agent is bone morphogenetic protein.

27. A sintered glass scaffold comprising glass fibers, wherein the glass fibers have a coating of one or more biocompatible polymers or copolymers, wherein the scaffold is a carrier for at least one bioactive agent, and wherein the bioactive agent is bone morphogenetic protein.

28. The scaffold of claim 1 or 5, wherein the compressive strength of the scaffold is from about 5 to about 25 MPa.

29. The scaffold of claim 1 or 5 wherein the compressive strength of the scaffold is over 20 MPa.

30. A sintered scaffold material comprising bioactive glass fibers sintered together to form the scaffold material,
    wherein the scaffold material has a porosity of between about 50 volume % and about 90 volume %,
    wherein the scaffold material has a pore size sufficient to allow ingrowth of tissue, and
    wherein the scaffold is attached to a biocompatible polymeric film.

31. The scaffold of claim 5, wherein the scaffold is attached to a biocompatible polymeric film.

32. A sintered scaffold material comprising bioactive glass fibers sintered together to form the scaffold material,
    wherein the scaffold material has a porosity of between about 50 volume % and about 90 volume %,
    wherein the scaffold is attached to a biocompatible polymeric film, and
    wherein the biocompatible polymeric film comprises a polymer or polymers selected from the group consisting of polyglycolide, polylactide, poly-β-hydroxybutyric acid, polydioxanone, polyvinylalcohol, polycsteramine, their copolymers and polymer blends thereof.

33. The scaffold of claim 1 or 5, wherein the scaffold is capable of promoting bone regeneration.

34. The scaffold of claim 1 or 5, wherein the fibers arc sintered together under compressive load.

35. The scaffold of claim 1 or 5, wherein the fibers are sintered together in a mold form.

36. A sintered scaffold material comprising bloactive glass fibers sintered together to form the scaffold material,
    wherein the scaffold material has a porosity of between about 50 volume % and about 90 volume %, and
    wherein the fibers form a mat which is attached to a membrane.

37. A sintered glass scaffold comprising bioactive glass fibers sintered together to form the scaffold,
    wherein the fibers have a coating of one or more biocompatible polymers or copolymers, and
    wherein the biocompatible polymer is selected from the group consisting of polyglycolide, polylactide, poly-β-hydroxybutyric acid, polydioxanone, polyvinylalcohol, polyesteramine, their copolymers and polymer blends thereof.

38. A sintered glass scaffold comprising glass fibers sintered together to form the scaffold,
    wherein the fibers have a coating of one or more biocompatible polymers or copolymers,
    wherein the scaffold is attached to a biocompatible polymeric film, and
    wherein the biocompatible polymeric film comprises a polymer or polymers selected from the group consisting of polyglycolide, polylactide, poly-β-hydroxybutyric acid, polydioxanone, polyvinylalcohol, polyesteramine, their copolymers and polymer blends thereof.

39. A sintered glass scaffold comprising glass fibers sintered together to form the scaffold,
    wherein the fibers have a coating of one or more biocompatible polymers or copolymers, and
    wherein the fibers form a mat which is attached to a membrane.

* * * * *

UNITED STATES PATENT AND TRADEMARK OFFICE
CERTIFICATE OF CORRECTION

PATENT NO.       : 7,241,486 B2
APPLICATION NO.  : 09/981676
DATED            : July 10, 2007
INVENTOR(S)      : Eija Marjut Pirhonen It is certified that error appears in the above-identified patent and that said Letters Patent is hereby corrected as shown below:

Title Page, Item (73) Assignee:

"Inion Ltd., Tampere (FI)", should be deleted

Signed and Sealed this
Sixth Day of December, 2011

David J. Kappos
*Director of the United States Patent and Trademark Office*